(12) United States Patent
Frach et al.

(10) Patent No.: US 7,723,694 B2
(45) Date of Patent: May 25, 2010

(54) DIGITAL SILICON PHOTOMULTIPLIER FOR TOF-PET

(75) Inventors: Thomas Frach, Aachen (DE); Klaus Fiedler, Aachen (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 379 days.

(21) Appl. No.: 11/467,670

(22) Filed: Aug. 28, 2006

(65) Prior Publication Data

US 2008/0203309 A1      Aug. 28, 2008

(51) Int. Cl.
*G01T 1/208* (2006.01)
(52) U.S. Cl. .................................. 250/370.11
(58) Field of Classification Search ............. 250/370.11
See application file for complete search history.

(56) References Cited

U.S. PATENT DOCUMENTS

| | | | | |
|---|---|---|---|---|
| H12 H | * | 1/1986 | Bennett et al. ......... | 250/363.09 |
| 5,777,335 A | * | 7/1998 | Mochizuki et al. ..... | 250/370.09 |
| 6,114,703 A | | 9/2000 | Levin et al. | |
| 6,541,752 B2 | | 4/2003 | Zappa et al. | |
| 6,781,133 B2 | | 8/2004 | Karplus et al. | |
| 2003/0012731 A1 | * | 1/2003 | Suddarth et al. ........... | 424/1.49 |
| 2005/0012033 A1 | | 1/2005 | Stern et al. | |
| 2006/0163485 A1 | * | 7/2006 | Stearns et al. .......... | 250/363.03 |

FOREIGN PATENT DOCUMENTS

| | | | |
|---|---|---|---|
| EP | 0 706 065 | A2 | 4/1996 |
| WO | WO 2004/044613 | A2 | 5/2004 |
| WO | WO 2004054235 | A1 * | 6/2004 |
| WO | 2004 099865 | A2 | 11/2004 |
| WO | WO 2004/095068 | A1 | 11/2004 |
| WO | WO 2005/017598 | A1 | 2/2005 |

OTHER PUBLICATIONS

Moehrs et al. A small-animal PET design using SiPMs and Anger logic with intrinsic DOI, 2004 IEEE Nuclear Science Symposium Conference Record, vol. 6 (Oct. 2004), pp. 3475-3479.*

Herbert, D. J., et al.; First Results of Scintillator Readout with Silicon Photomultiplier; 2004; IEEE Nuclear Science Symposium Conf. Record; pp. 4185-4189.

(Continued)

*Primary Examiner*—David P Porta
*Assistant Examiner*—Shun Lee

(57) ABSTRACT

A radiation detector includes an array of detector pixels each including an array of detector cells. Each detector cell includes a photodiode biased in a breakdown region and digital circuitry coupled with the photodiode and configured to output a first digital value in a quiescent state and a second digital value responsive to photon detection by the photodiode. Digital triggering circuitry is configured to output a trigger signal indicative of a start of an integration time period responsive to a selected number of one or more of the detector cells trinsitioning from the first digital value to the second digital value. Readout digital circuitry accumulates a count of a number of transitions of detector cells of the array of detector cells from the first digital state to the second digital state over the integration time period.

27 Claims, 10 Drawing Sheets

OTHER PUBLICATIONS

Otte, A. N., et al.; New Results from a Test of Silicon Photomultiplier as Readout for PET; 2004; IEEE Nuclear Science Symposium Conf. Record; pp. 3738-3742.

Aull, B.F. et al, "Geiger-Mode Avalanche Photodiodes for Three-Dimesioinal Imaging," Lincoln Laboratory Journal, vol. 13, No. 2, Oct. 30, 2002.

Georgievskya, E.A., "The solid-state silicon photomultiplier for a wide range of applications," Proc. of SPIE, 5126:37-42, May 27-31, 2002.

Golovin, V. et al., Novel type of avalanche photodetector with Geiger mode operation,: Nuclear Instruments and Methods in Physics Research A 518, 560-564, Feb. 1, 2004.

Sadygov, Z.Y. et al., "Avalanche Semiconductor Radiation Detectors," IEEE Trans. on Nuclear Science, 63(3), 1009-1013, Jun. 1996.

Saveliev, V., "The recent development and study of silicon photomultiplier," Nuclear Instruments and Methods in Physics Research A, 535:528-532, Aug. 25, 2004.

* cited by examiner

DIGITAL SILICON PHOTOMULTIPLIER FOR TOF-PET

CROSS REFERENCE TO RELATED APPLICATIONS

This application is a Continuation of PCT application number PCT/IB2006/051089 filed Apr. 10, 2006 which claims the benefit of U.S. provisional application Ser. No. 60/674,034 filed Apr. 22, 2005 and U.S. provisional application Ser. No. 60/682,246 filed May 18, 2005, which are all incorporated herein by reference.

BACKGROUND

The following relates to the radiation detection arts. It particularly relates to high-speed radiation detectors for positron emission tomography (PET), especially time-of-flight (TOF) PET, and will be described with particular reference thereto. However, the following relates more generally to radiation detectors for single photon emission computed tomography (SPECT), computed tomography (CT), and so forth, as well as to high-speed radiation detectors for other applications such as astronomy.

In conventional PET, a radiopharmaceutical is administered to a human patient or other imaging subject. The radiopharmaceutical produces radiation decay events that emit positrons, which travel a very short distance before rapidly interacting with an electron of the surrounding imaging subject in an electron-positron annihilation event to produce two oppositely directed gamma rays. The gamma rays are detected by radiation detectors surrounding the imaging subject as two substantially simultaneous radiation detection events that define a line of response (LOR) therebetween. Typically, the radiation detectors include scintillators that produce a burst or scintillation of light responsive to each gamma ray detection, and an array of photomultiplier tubes (PMT's) optically coupled with the scintillators that convert the light bursts into corresponding electrical signals. In some PET scanners, the PMT's are replaced by photodiodes that produce analog electrical currents proportional to the intensity of the light bursts.

Although the gamma rays are detected "substantially simultaneously", if one of the two involved radiation detectors is closer to the electron-positron annihilation event than the other radiation detector, then there will be a small time difference between the two radiation detection events. Since gamma rays travel at the speed of light, this time difference between detections is typically around a few nanoseconds or less. In TOF-PET, the radiation detectors operate at sufficiently high speed to enable measurement of this small time-of-flight difference, which is then used to localize the electron-positron annihilation event along the LOR.

Accordingly, for TOF-PET the radiation detectors should have sub-nanosecond temporal resolution. PMTs are generally fast enough to perform TOF-PET imaging; however, PMTs are bulky, require high voltage biasing, and are not well-suited for small pixel sizes desirable for high resolution. Conventional photodiodes are fast enough for TOF-PET, but lack internal amplification, leading to poor signal-to-noise ratios. To get sufficient signal with a conventional photodiode, a charge-sensitive amplifier is typically employed to integrate the signal, which limits the bandwidth. Avalanche photodiodes can also be used; however, avalanche photodiodes typically suffer from high noise levels and high temperature and bias sensitivity in the gain.

To address these difficulties, silicon photomultiplier (SiPM) detectors have been proposed, for example in: E. A. Georgievskya et al., "The solid state silicon photomultiplier for a wide range of applications", $17^{th}$ Int'l Conf. on Photo-electronics and Night Vision Devices, Proceedings of SPIE vol. 5126 (2003); Golovin et al., "Novel type of avalanche photodetector with Geiger mode operation", Nuclear Instruments & Methods in Physical Research A, volume 518, pages 560-64 (2004). These SiPM detectors use a pixelated array of small avalanche photodiodes biased in the breakdown region and interconnected in parallel. The output is the analog sum of the currents of parallel-interconnected avalanche photodiodes operating in limited Geiger-mode. Each detected photon in the SiPM detector adds on the order of $10^6$ electrons to the output current of the SiPM. The Geiger discharge responsive to photon detection is fast, providing sharp rising edges of the signal that facilitate precise time measurements. Energy- and temporal-resolution scales with $1/\sqrt{N}$ where N is the number of firing cells.

The SiPM device has certain disadvantages. The analog current produced by a photon detection is affected by bias voltage, operating temperature, and critical circuit parameters such as the quenching resistance value. These factors can change the analog current produced by each photon detection, thus limiting the energy resolution of the SiPM. The analog configuration also has the disadvantages of producing high dark counts and allowing faulty avalanche photodiodes to substantially limit detector device manufacturing yield.

The following contemplates improved apparatuses and methods that overcome the aforementioned limitations and others.

BRIEF SUMMARY

According to one aspect, a detector pixel is disclosed for use in conjunction with a scintillator that converts a radiation particle to a burst of light. An array of detector cells is provided. Each detector cell includes a photodiode biased in a breakdown region and digital circuitry coupled with the photodiode. The digital circuitry is configured to output a first digital value in a quiescent state and a second digital value responsive to detection of a photon by the photodiode. Digital triggering circuitry is configured to output a trigger signal indicative of a start of an integration time period responsive to a selected number of one or more of the detector cells transitioning from the first digital value to the second digital value. Readout digital circuitry accumulates a count of a number of transitions of detector cells of the array of detector cells from the first digital state to the second digital state over the integration time period.

In some embodiments, digital timestamp circuitry is configured to output a digital timestamp associated with the count. The digital timestamp is based on a time of the trigger signal relative to a time reference signal.

According to another aspect, a radiation detector includes a scintillator and an array of detector pixels as set forth in the previous paragraph arranged to receive bursts of light produced by the scintillator in response to received radiation.

According to another aspect, a time-of-flight positron emission tomography (TOF-PET) imaging system is disclosed. A plurality of radiation detectors as set forth in the previous two paragraphs are disposed to detect gamma rays emitted from an imaging region. Gamma ray pair detection circuitry identifies two substantially simultaneous gamma ray detections by two of the radiation detectors. A line of response processor determines a spatial line of response connecting the two gamma ray detections. A time of flight processor localizes a positron-electron annihilation event along the line of response based on a time difference between the two substantially simultaneous gamma ray detections.

According to another aspect, a method is performed in conjunction with a scintillator that converts a radiation particle to a burst of light. Digital circuitry is switched from a first digital value to a second digital value responsive to detection of a photon by a photodiode biased in a breakdown region by the digital circuitry to define a switching event. A trigger signal indicative of a start of an integration time period is generated responsive to a selected number of one or more said switching events associated with a plurality of said photodiodes. A count of switching events associated with the plurality of said photodiodes is accumulated over the integration time period.

In some embodiments, the method further includes generating a digital timestamp associated with the accumulating over the integration time period. The digital timestamp is based on a time of generation of the trigger signal and a reference time signal.

According to another aspect, a radiation detector is disclosed, including a scintillator and circuitry for performing the method set forth in the previous paragraph.

One advantage resides in providing high data-rate radiation detection for TOF-PET, single photon emission computed tomography (SPECT), transmission computed tomography (CT), astronomy, and other applications.

Another advantage resides in providing a digital radiation detector output.

Another advantage resides in providing a digitally timestamped detector output.

Another advantage resides in providing improved spatial detector resolution.

Another advantage resides in improved detector device manufacturing yield with low sensitivity to temperature, bias voltage, and process parameters.

Numerous additional advantages and benefits will become apparent to those of ordinary skill in the art upon reading the following detailed description.

BRIEF DESCRIPTION OF THE DRAWINGS

The invention may take form in various components and arrangements of components, and in various process operations and arrangements of process operations. The drawings are only for the purpose of illustrating preferred embodiments and are not to be construed as limiting the invention.

DETAILED DESCRIPTION OF THE PREFERRED EMBODIMENTS

Figure 1:
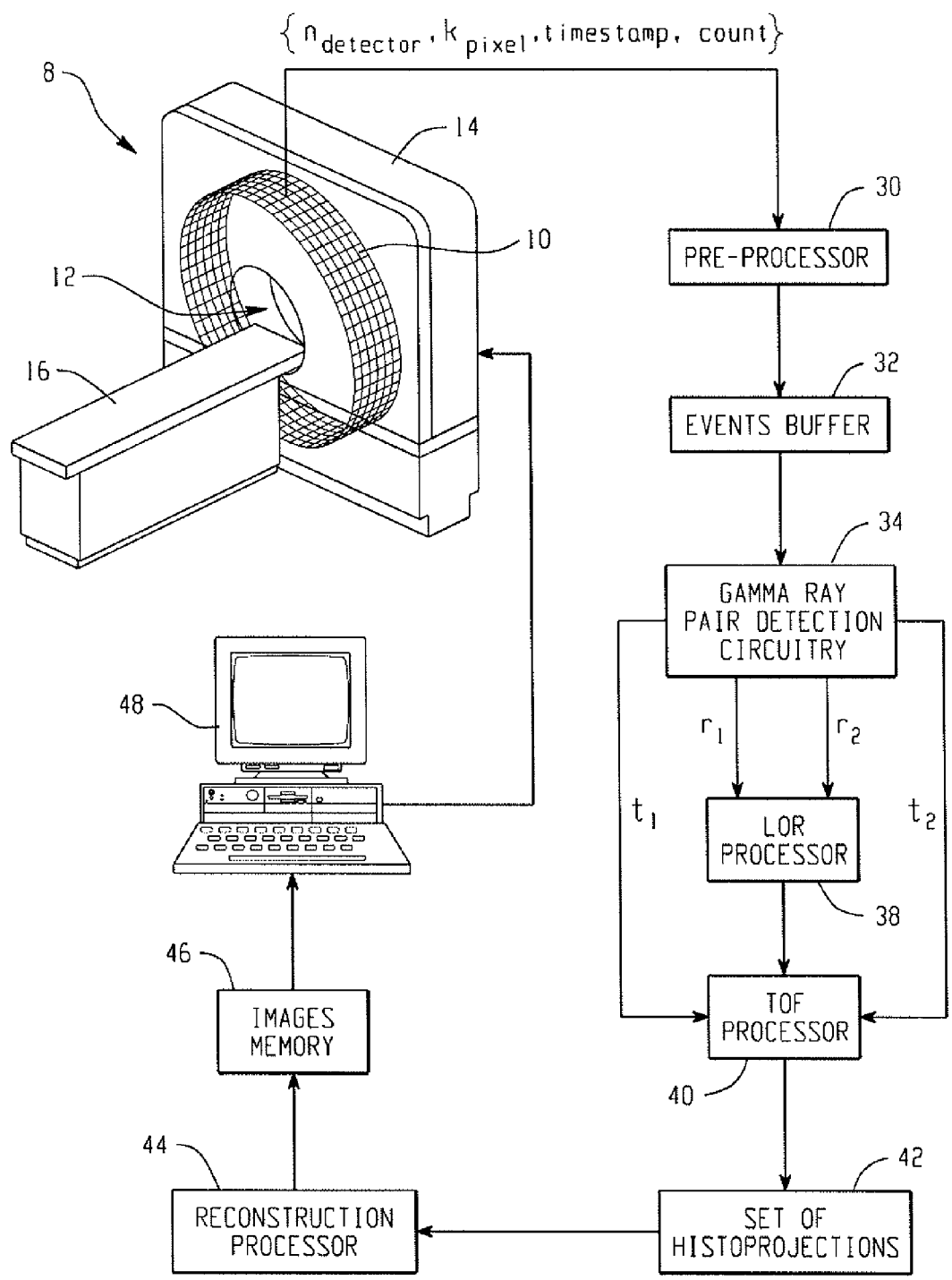
FIG. 1 diagrammatically shows a TOF-PET system employing high-speed ixilated digital radiation detectors.

With reference to FIG. 1, a time-of-flight positron emission tomography (TOF-PET) scanner 8 includes a plurality of radiation detectors 10 arranged to view an imaging region 12. In FIG. 1, the plurality of radiation detectors 10 are arranged in several rings of detectors along an axial direction; however, other arrangements of radiation detectors can be used. Moreover, it is to be appreciated that the plurality of radiation detectors 10 is diagrammatically illustrated; typically the radiation detectors are housed within a housing 14 of the scanner 8 and thus are not visible from the outside, and typically each ring of radiation detectors includes hundreds or thousands of radiation detectors. In some PET scanners, only a single ring of radiation detectors is provided, in others, two, three, four, five, or more rings of radiation detectors are provided. It should be appreciated that detector heads can be used in place of the detector ring structure shown in the Figures. The TOF-PET scanner 8 includes a couch 16 or other support for positioning a human patient or other imaging subject in the imaging region 12. Optionally, the couch 16 is linearly movable in the axial direction generally transverse to the rings of radiation detectors 10 to facilitate acquisition of three-dimensional imaging data. Additionally or alternatively, the imaging subject can be held stationary, and the plurality of rings of radiation detectors used to acquire three-dimensional TOF-PET imaging data. In yet other embodiments, only a single ring of detectors is provided, the imaging subject remains stationary, and the resulting image is two-dimensional.

A suitable radiopharmaceutical is administered to the patient or other imaging subject prior to initiation of TOF-PET imaging. The radiopharmaceutical includes a radioactive substance that undergoes radioactive decay events that emit positrons. The positrons rapidly annihilate with nearby electrons of the imaging subject. The resulting positron-electron annihilation event produces two oppositely directed gamma rays having energies of 511 keV. The gamma rays travel at the speed of light, i.e. $\sim 3 \times 10^8$ meters/sec. Since the imaging region 12 typically has a diameter or other characteristic dimension of about two meters or less, the time-of-flight for a gamma particle from the position of the positron-electron annihilation event to one of the detectors of the plurality of radiation detectors 10 is about a few nanoseconds or less. Thus, the two oppositely directed gamma rays strike two of the radiation detectors substantially simultaneously.

Figure 2:
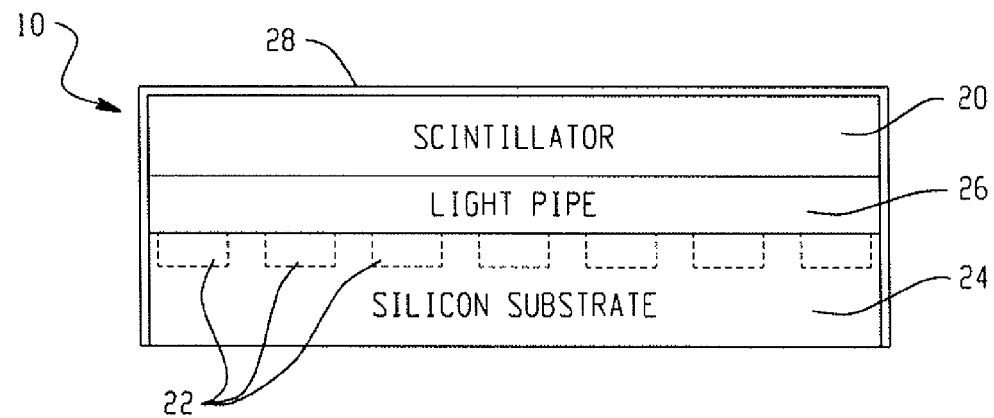
FIG. 2 diagrammatically shows a cross-sectional view of one of the ixilated digital radiation detectors of the TOF-PET system of FIG. 1.

With continuing reference to FIG. 1 and with further reference to FIG. 2, each radiation detector 10 includes a scintillator 20 that produces a scintillation or burst of light when the gamma ray strikes the scintillator 20. The burst of light is received by an array of detector pixels 22 monolithically disposed on a silicon substrate 24. As will be described, the detector pixels 22 are digital detector pixels that output values including a digital representation of a count of photons (denoted "count" in FIG. 1) and a digital representation of a timestamp (denoted "timestamp" in FIG. 1) indicative of when the burst of light corresponding to the scintillation event was detected by the detector pixel 22. Moreover, the plurality of radiation detectors 10 outputs indexing information including, for example, a detector index (denoted "$n_{detector}$" in FIG. 1) indicating which of the radiation detectors 10 output the radiation detection event, and a detector pixel index (denoted "$k_{pixel}$" in FIG. 1) indicating which detector pixel or pixels of that radiation detector detected the burst of light corresponding to the radiation detection event. The scintillator 20 is selected to provide high stopping power for 511 keV gamma rays with rapid temporal decay of the scintillation burst. Some suitable scintillator materials are LSO, LYSO, MLS, LGSO, LaBr and mixtures thereof. It should be appreciated that other scintillator materials can also be used. Although FIG. 2 shows the scintillator 20 as a single crystal, an array crystals can instead be used. Additionally, an optional planar light pipe 26 can be interposed between the scintillator 20 and the detector pixels 22 to improve transmission of photons of the scintillation light burst to the detector pixels 22. The scintillator 20 and optional light pipe 26 are optionally encased in a reflective coating 28 which directs scintillation light toward the pixels 22.

With continuing reference to FIG. 1, the digital data concerning radiation detection events are processed by a pre-processor 30 that performs selected data processing. For example, if a scintillation event is detected by a plurality of detector pixels, then the pre-processor 30 can employ Anger logic or other processing to identify spatial coordinates r for each radiation detection event and to estimate an energy of the detected radiation particle. The resulting spatial and energy information for each radiation detection event is stored in an events buffer 32. In other embodiments, the scintillator layer is divided into scintillator tiles sized to correspond with the detector pixels, and each detector pixel is optically coupled with a single scintillator tile. For example, each scintillator tile may include a reflective coating similar to the reflective coating 28 to channel the scintillation photons to the coupled pixel.

A gamma ray pair detection circuitry 34 processes the radiation detection events to identify pairs of substantially simultaneous gamma ray detections belonging to corresponding electron-positron annihilation events. This processing can include, for example, energy windowing (that is, discarding radiation detection events outside of a selected energy filtering window disposed about 511 keV) and coincidence-detecting circuitry (that is, discarding radiation detection event pairs temporally separated from each other by greater than a selected time filtering interval).

When a gamma ray pair is identified, a line-of-response (LOR) processor 38 processes the spatial information pertaining to the two gamma ray detection events (for example, with the two events represented by spatial coordinates $r_1$ and $r_2$, respectively, as computed by the pre-processing 30) to identify a spatial line of response (LOR) connecting the two gamma ray detections. Since the two gamma rays emitted by a positron-electron annihilation event are oppositely spatially directed, the electron-positron annihilation event is known to have occurred somewhere on the LOR.

In TOF-PET, the radiation detectors 10 have sufficiently high temporal resolution to detect a time-of-flight difference between the two "substantially simultaneous" gamma ray detections. A time-of-flight processor 40 analyzes the time difference between the times (denoted "$t_1$" and "$t_2$" in FIG. 1) of the two gamma ray detection events to localize the positron-electron annihilation event-along the LOR. The result, accumulated for a large number of positron-electron annihilation events, is a set of histoprojections 42. A reconstruction processor 44 reconstructs the set of histoprojections 42 into a reconstructed image using any suitable reconstruction algorithm, such as filtered backprojection or iterative backprojection with correction. The resulting reconstructed image is stored in an images memory 46, and can be displayed on a user interface 48, printed, stored, communicated over an intranet or the Internet, or otherwise used. In the illustrated embodiment, the user interface 48 also enables a radiologist or other user to control the TOF-PET scanner 8; in other embodiments, a separate controller or control computer may be provided.

Figure 3:
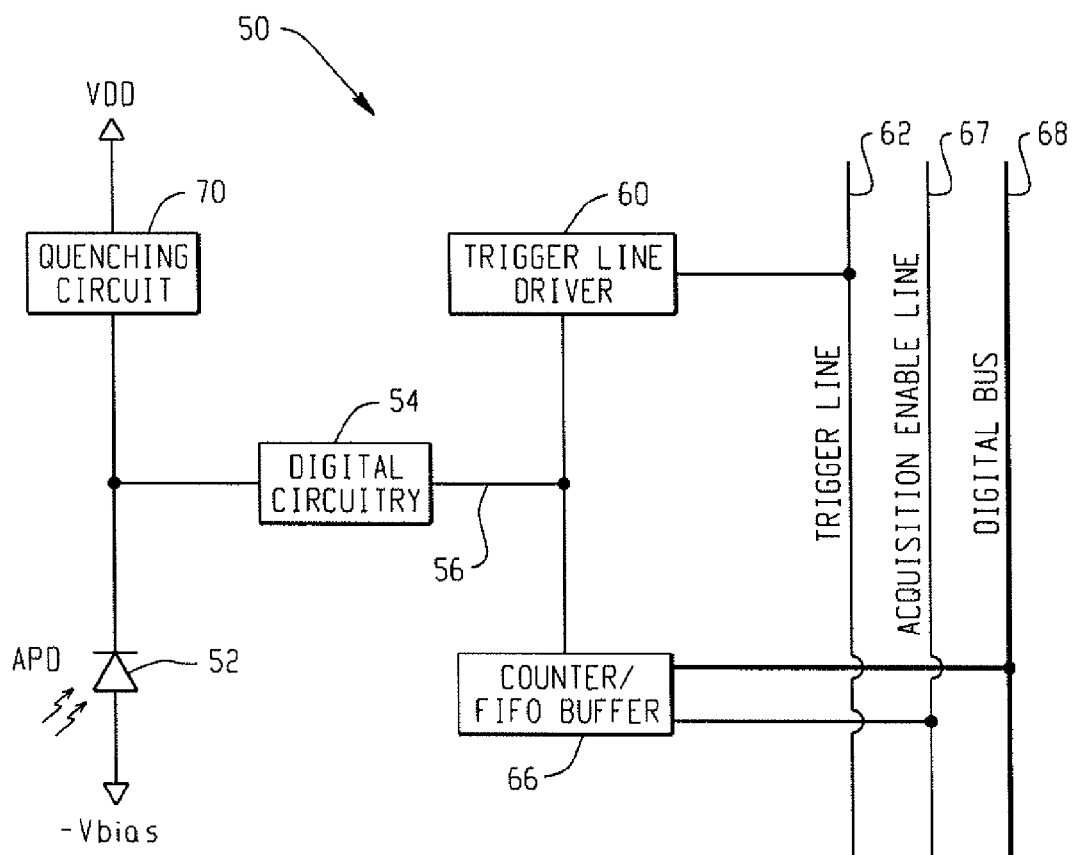
FIG. 3 shows a general circuit diagram of one of the detector cells of the ixilated digital radiation detector.

With reference to FIG. 3, each pixel 22 of the radiation detector 10 includes an array of detector cells 50; FIG. 3 shows a general circuit diagram of one such detector cell 50. A photodiode 52 is biased in a breakdown region and serves as an input to digitizing circuitry 54. An output 56 of the digitizing circuitry 54 has a first digital value corresponding to a quiescent state, and transitions to a second digital value responsive to detection of a photon by the photodiode 52. When the first photon of a scintillation burst is detected, the switching of the output 56 from the first digital value to the second digital value activates an open collector trigger line driver 60 which causes a trigger signal to be applied to a common trigger line or bus 62. The trigger signal in turn initiates a photon counter/FIFO buffer 66 (where FIFO="first in, first out") that counts the switchings of the digitizing circuitry 54 from the first digital value to the second digital value over an integration time period started by the trigger signal. In some other embodiments, an acquisition enable line 67 initiates the photon counter 66. A quenching circuit 70, which may be either active or passive, limits current through the photodiode 52 and is configured to facilitate transition the biasing circuitry from the second digital value back to the first digital value. Thus, the detector cell 50 may count more than one photon if the detector cell 50 is quenched back to the quiescent first digital value before the integration time period expires. The final count stored in the photon counter/FIFO buffer 66 is accessible via a digital bus 68.

The photodiode 52 is suitably biased in a Geiger-mode type of operation. When the photodiode 52 breaks down, large amount of charge (for example, about $10^6$ electrons per received detection in some photodiodes) is generated through the avalanche breakdown process. This charge is transported primarily through the quenching circuit 70, which has an effective resistance of typically several hundred kilo-ohms to limit the current flowing through the photodiode 52. With the current thus limited, charge remaining in the photodiode 52 distributes spatially to reduce the electric field in the avalanche region of the photodiode 52. This screening quenches the avalanche process and causes remaining carriers to be transported by drift out of the avalanche/depletion zone, causing recovery of the photodiode 52. Typically, the photodiode 52 includes a guard ring (not shown) around the periphery that prevents avalanche breakdown at the edges of the photodiode 52. The guard ring structure suitably acts like an ordinary reverse-biased PN diode with internal fields too low for the avalanche breakdown to occur.

Figure 4A:
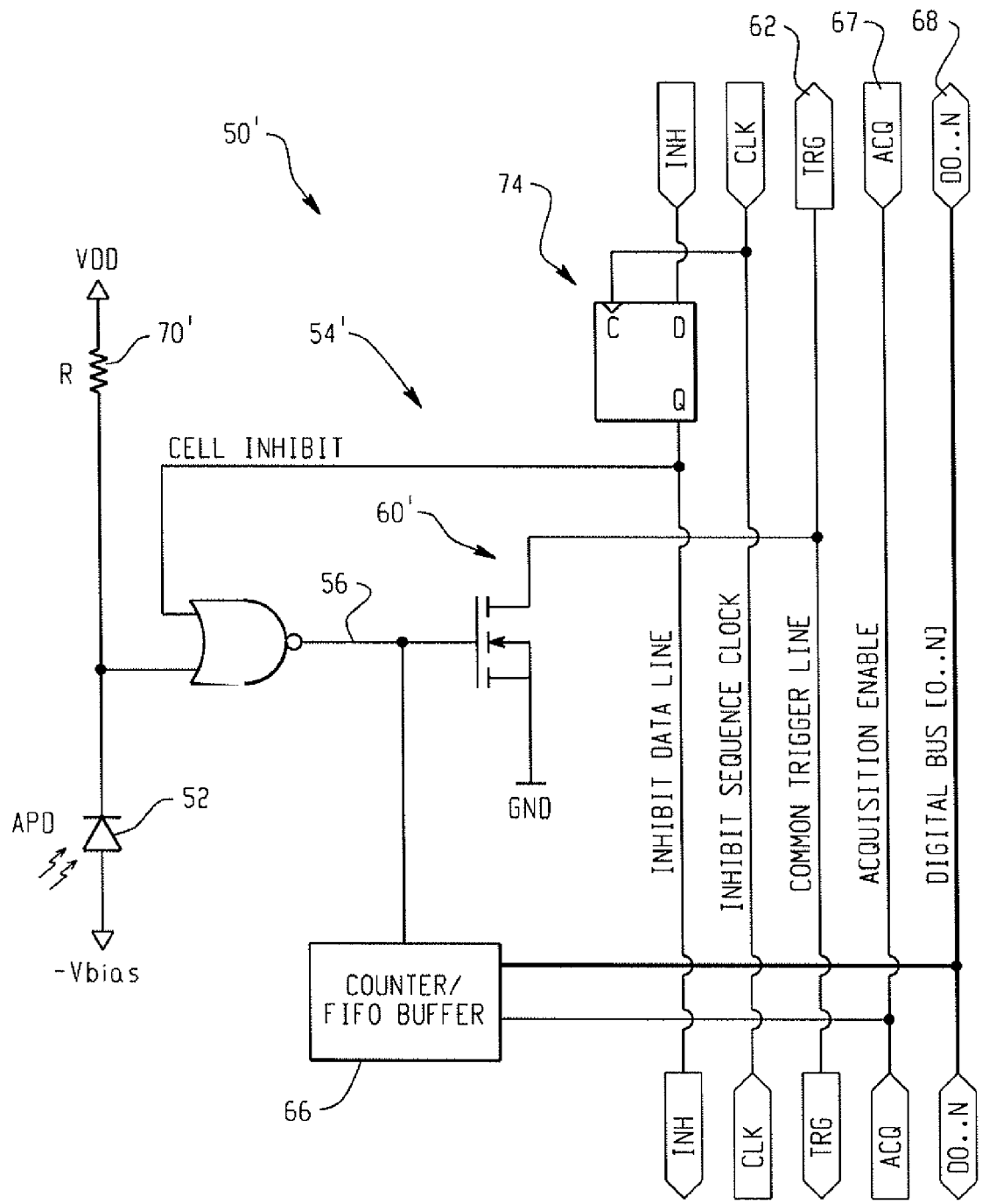
FIG. 4A shows a more detailed circuit diagram of one embodiment of one of the detector cells.

With reference to FIG. 4A, a more detailed circuit diagram of one example embodiment detector cell 50' is described. This embodiment includes a passive quenching circuit 70' embodied as a quenching resistor. On photon detection, the junction of the photodiode 52 breaks down and an electric current starts to flow through the photodiode 52 and the quenching resistor 70'. This current causes a voltage drop across the resistor 70', thus lowering the potential on the inverter input. The voltage difference relative to $V_{DD}$ should be large enough to drive the inverter output into a "high" state. The switching characteristics of the inverter can be optimized by adjusting the transistor widths. The inverter output returns to a "low" state automatically when the photodiode 52 recovers from the breakdown.

With continuing reference to FIG. 4A, the detector cell 50' further implements inhibit logic 74 which does not switch off a faulty detector cell completely, but rather prevents faulty detector cells from generating false triggers. Faulty detector cells will generate excess currents which are taken into account in the trigger validation circuit (described later). When using the detector cells 50', the trigger line 62 is tied to a "high" level via a pull-up resistor (not shown in FIG. 4A). This way, the triggers from all the detector cells 50' are logically "or"-ed together and the trigger line 62 is pulled down by that detector cell which detects the first photon.

Figure 4B:
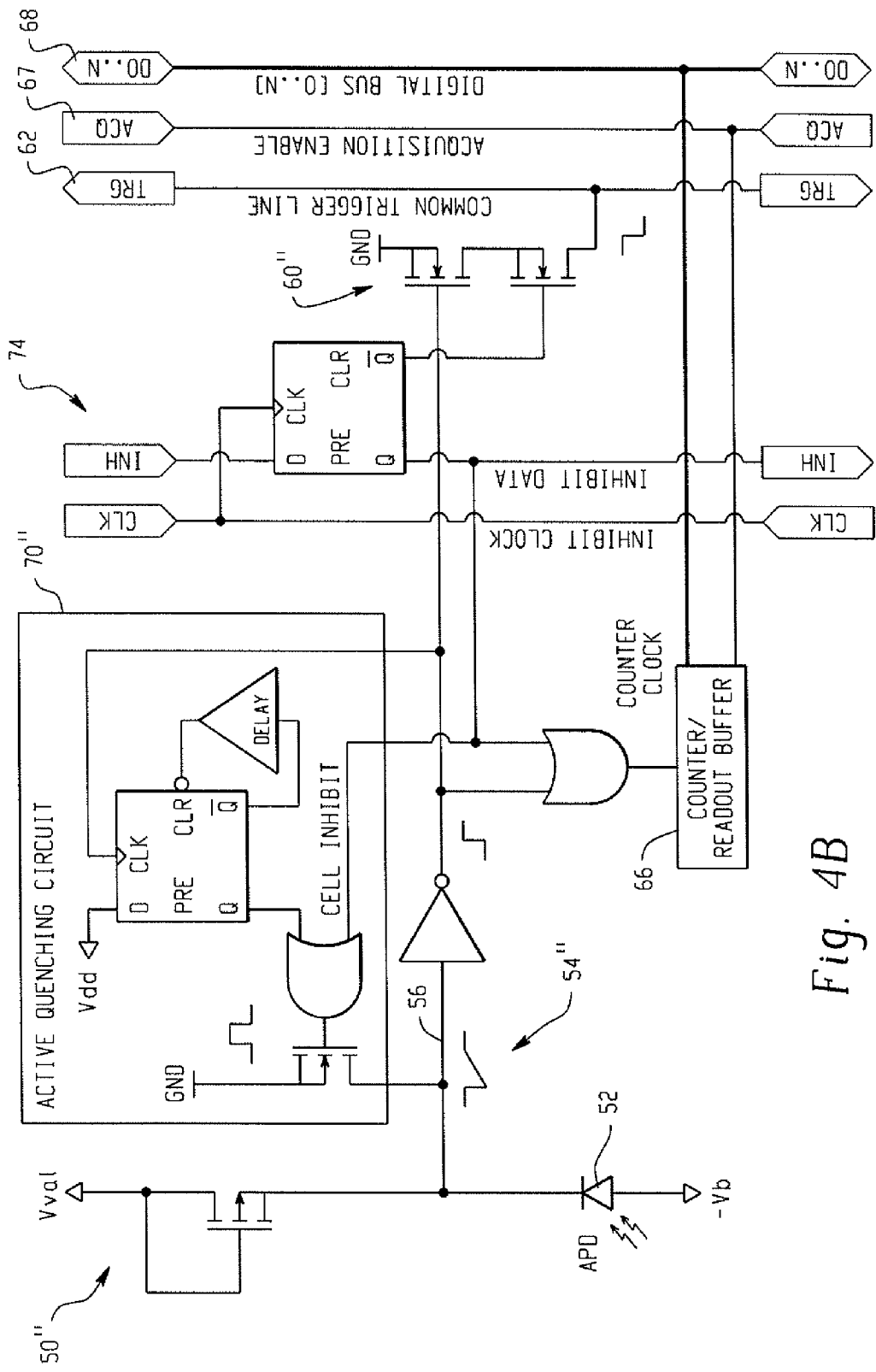
FIG. 4B shows a more detailed circuit diagram of another embodiment of one of the detector cells.

With reference to FIG. 4B, a more detailed circuit diagram of another example embodiment detector cell 50" is described, which includes an active quenching circuit 70" to speed up the discharge of the junction capacitance of the photodiode 52 to return to the quiescent level, thus reducing the recovery time of the photodiode 52. Shorter recovery times are expected to lead to higher sensitivity, since a given detector cell 50" is more likely to count more than one photon during the integration time period when it recovers quickly, and are expected to lead to higher dynamic range and better energy resolution of the detector cell 50". The photon counter 66 is enabled either by the trigger line 62 or a dedicated line if a hierarchical trigger network is used, which is pulled down by that detector cell which detects the first photon, and is held down by main pixel logic (not shown in FIG. 4B) for the integration time period. The number of detected photons accumulated by the photon counter 66 is transferred from the photon counter 66 to a buffer or other digital storage (not shown in FIG. 4B) on the rising edge of the trigger line 62 or a dedicated readout line. Subsequently, the counter 66 is reset automatically, for example by the low level of the inverted and delayed signal on the trigger line 62, in preparation for the next scintillation burst detection event. In this arrangement, the dead time between integration time periods can be as low as the buffer transfer time plus the reset time of the counter 66, which in some embodiments is expected to be less than one nanosecond for CMOS implementations. The detector cell 50" of FIG. 4B also includes inhibit logic 74 to prevent false triggers from faulty detector cells.

Figure 5:
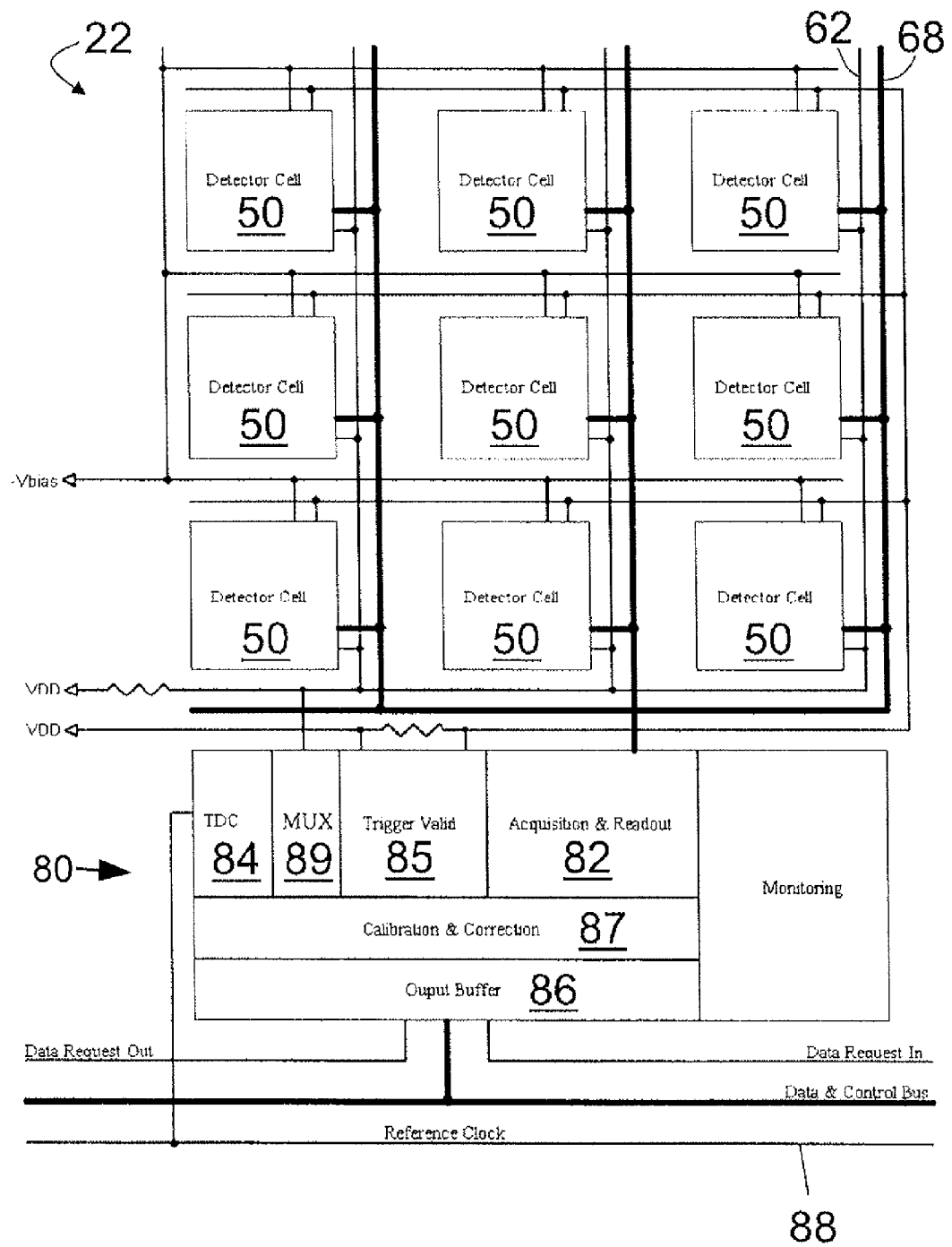
FIG. 5 shows a circuit diagram of one pixel of the ixilated digital radiation detector.

With reference to FIG. 5, each pixel 22 of the radiation detector 10 includes a two-dimensional array of detector cells 50 and associated pixel-level digital pixel logic 80. Digital readout circuitry for the pixel 22 includes pixel-level digital acquisition and readout circuitry 82 and associated circuitry at the detector cell level.

With reference to FIGS. 3 and 5, the digitizing circuitry 54 of each detector cell 50 provides a threshold-based binary digital output indicating whether or not the photodiode 52 of that detector cells has entered breakdown. The digital circuitry 54 outputs a first binary value when the photodiode 52 is in its quiescent state, and transitions to a second binary value when the photodiode current increases beyond a threshold value indicative of photon detection. The signal of each photodiode 52 is thus digitized at the level of the detector cell 50. Readout is performed by the pixel-level logic counting the digital transitions of the detector cells to produce a digital pixel output indicative of the number of detected photons. Compared with the summing of analog photodiode currents to generate an analog pixel output as is done in analog SiPMs, the digitize-and-count method of FIGS. 3 and 5 is far less sensitive to bias variations, operating temperature variations, tolerances in components of the quenching circuit 70, or so forth. As long as these secondary effects do not cause erroneous switching or missed switching of the thresholding digital circuitry 54, they generally do not affect the energy resolution of the detector cell 50.

In some readout approaches, the detector cells 50 are addressed like in a standard memory block, using address decoders for the rows and columns of the array of detector cells 50. This solution provides a sequential readout of the cell data, in which case the pixel-level readout circuitry 82 can be a simple digital accumulator. In other readout approaches, cells lines are read out in parallel, with each line having its own accumulator for the partial sum, and the partial sums are added in a parallel adder tree. In yet other readout approaches, the adders are incorporated into the detection cells, so that the sum of the whole line is obtained while clocking the data out and the line sum is read out from the last detector cell in the line. As the summation in this latter readout approach can be pipelined, the readout architecture is fast, allowing short readout intervals.

If the detector cell-level photon counters 66 or counters of the pixel-level readout circuitry 82 are likely to saturate, then the counters should not be allowed to wrap around. For example, a four-bit counter counting from 0 . . . 15 should not be allowed to increment from 15 back to 0. By avoiding wrap-around, saturation of the pixel 22 can be detected when the counter reads its highest value (e.g., 15 for a four-bit counter). The number of bits for avoiding wrap-around depends solely on the minimum anticipated cell recovery time and the maximum length of the integration period. While the integration window is a design parameter, the cell recovery time is of a statistical nature, as photon detection probability is a function of the slowly rising over-voltage during cell recovery. In an actively quenched cell however, a minimum recovery time is defined by the monoflop delay. Thus, in this case, it is possible to design the counter wide enough to avoid overflow. The digital bus 68 can be either a parallel or a serial bus, depending on space and time constraints.

With continuing reference to FIG. 5, the digital pixel logic 80 further includes trigger digital circuitry 84, trigger validation circuitry 85, and an output buffer 86 that stores the photon count of the pixel 22. The trigger digital circuitry 84 accesses a reference clock 88 (shown as an electrical trace that is connected to a suitable oscillator or other clocking device not shown in FIG. 5) to provide a time reference for the trigger digital circuitry 84. The trigger digital circuitry 84 determines the time stamp of a radiation detection event in a global (for example, scanner) time frame. The trigger digital circuitry modules 84 of all the pixels 22 of the scanner run synchronously at a precision of preferably less than 100 ps. The reference signal 88 is used to synchronize the trigger digital circuitry modules 84 of the pixels, providing them with a common time base for the entire scanner. In some embodiments, the integration time period is a fixed time interval starting at the occurrence of the trigger signal. In other embodiments, the integration time period is dynamically terminated when the rate of new counts decreases below a threshold value.

The trigger digital circuitry 84 is also preferably configured to output the digital timestamp (see FIG. 1) associated with the count. The digital timestamp is based on a time of the trigger signal output by the trigger line driver 60 of the first one of the detector cells 50 that detects a photon from a scintillation burst. The pixel logic 80 optionally still further includes data correction registers and inhibit sequence drivers. Automated test and calibration circuitry 87 is also optionally implemented by the pixel logic 80. In one test/calibration method, the (lark count rate of the pixel 22 (possibly including background counts produced by intrinsic radioactivity of the scintillator 20) is monitored. In another test/calibration method, an external excitation from a test charge injected into the detector cells 50 is used to test and calibrate the pixel 22.

With continuing reference to FIG. 5, it will be appreciated that due to dark currents, crosstalk, thermal excitations, or so forth, it is possible that one of the detector cells 50 may produce an inadvertent trigger signal starting an integration time period. The trigger validation circuitry 85 validates the trigger signal and aborts the integration if it is determined that the trigger signal was false. In one approach, the trigger validation circuitry 85 analyzes the current flowing through the bias network of the pixel 22. If the total current stays below a certain current threshold for a selected time interval (e.g. for 10 nanoseconds into the acquisition time period) as measured by a discriminator or other circuitry, then the acquisition is aborted and an automatic reset sequence is initiated in preparation for the next trigger. If the current exceeds the current threshold, the discriminator output will rise to a 'high' level and the acquisition will continue. In some embodiments, rather than using a fixed integration time period, the falling edge of the bias current discriminator is used to detect the end of the scintillation burst so as to adapt the integration time period to substantially match the end of the acquisition interval. This can suppress pile-up in high count rate applications. Another suitable method makes use of the fact that the probability of two thermally generated triggers inside a short time window decreases with the distance of the triggering cells since thermal triggers are generally not correlated. In contrast, the scintillation burst should act on detector cells 50 across the light-sensitive area of the pixel 22. Thus, the trigger validation circuitry 85 can analyze the triggers from individual detector cells 50, for example, and validate the trigger signal if two distant lines generate a trigger signal within a selected time window. Other approaches for trigger validation can also be used, such as employing a current sensor with adjustable discriminator set at a trigger threshold higher than the single photon level.

In some other embodiments, the counter 66 is triggered by the acquisition enable line 67. Triggering on the first photon can be problematic if there is a high background flux of photons unrelated to positron-electron annihilation events. This background can be the result of, for example, a secondary slow decay mode of the scintillator. In such cases, detector cells fire frequently, increasing the dead time of the pixel. To provide more robust counter initiating, at the detector cell level (FIG. 3, 4A, or 4B) the photon counter is enabled by the separate, 'acquisition enable' line 67 which is pulled down by the pixel logic on either the detection of the first photon (trigger line goes down) or by the discriminator of the trigger validation circuit 85 when the current through the bias network has exceeded the user-defined trigger level. This line defines the length of the integration window and is driven by the pixel logic. At the detector pixel level (FIG. 5), the trigger validation circuit 85 is extended to include a multiplexer 89 selecting either the trigger line 62 (for a single photon trigger) or the leading edge discriminator output (for multiple photon trigger) as the input to the time to digital converter/trigger validation circuits. The trigger validation circuit 85 is extended to provide the 'acquisition enable' signal 67 to the detector cells 50, 50', 50".

Alternatively, if triggering at single-photon level is not required, a suitable logic can be implemented to generate the trigger signal if a selected number of cells (trigger lines) become active at the same time. This implementation has the practical advantage requiring only digital components. However, in this case, the threshold is defined only statistically. In some other embodiments, the open collector driver is optionally omitted from the detector cells and a modified design is used in the trigger validation circuit.

Figure 6:
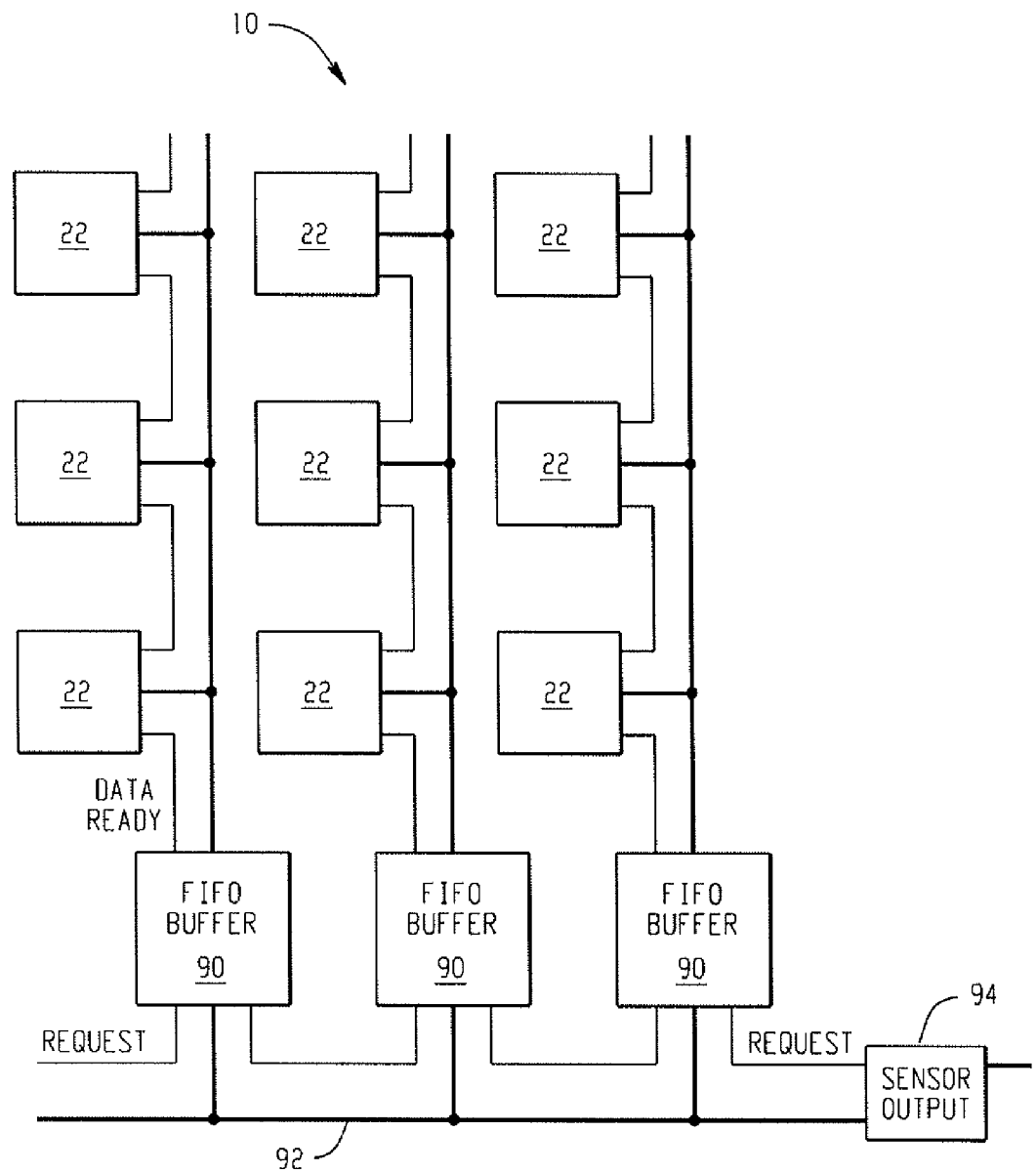
FIG. 6 shows a circuit diagram of one the ixilated digital radiation detectors.

With continuing reference to FIG. 5 and with further reference to FIG. 6, the pixels 22 are arranged in a two dimensional array to define the light sensitive surface of the pixelated radiation detector 10. The embodiment shown in FIG. 6 uses a pixel readout in which each line of pixels 22 is read out by FIFO buffers 90. The output buffers 90 each include tristate output buffers allowing the data to be transferred over a shared digital data bus 92. Optionally, the events are sorted according to their time stamps by the readout arbitration in the line output buffers 90 and also by the shared bus arbitration by output buffer 94, thus leading to a stream of event data which is sorted over time. This optional feature substantially simplifies the search for coincident events. A data request daisy-chain is suitably used for write access arbitration. The daisy chained sums are transferred to the radiation detector output buffer 94 for transfer off chip.

Figure 7:
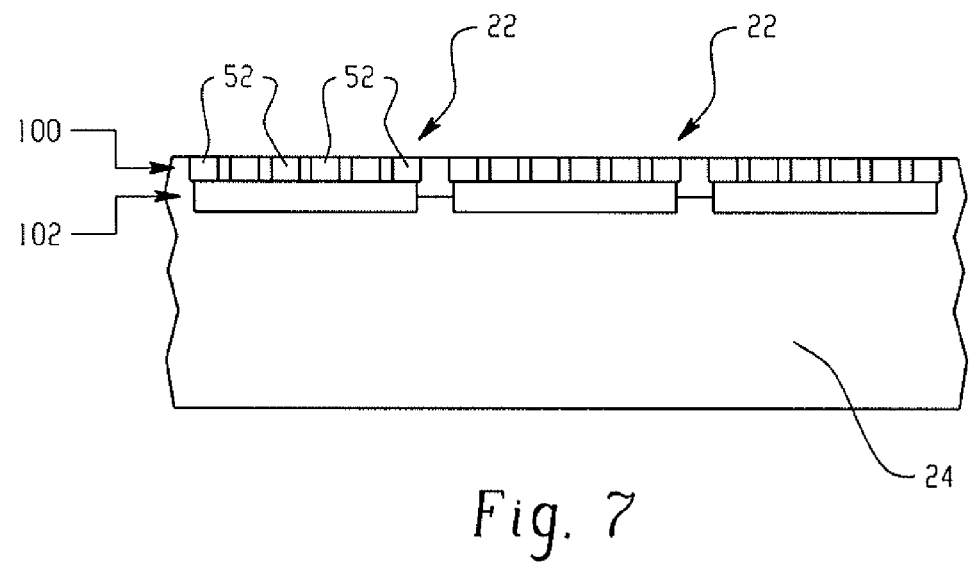
FIG. 7 shows a cross-sectional view of one physical layout embodiment of the ixilated digital radiation detector, in which the photodiodes define a photodiode layer and the digital circuitry is disposed in a digital circuitry layer separate from and electrically coupled with the photodiode layer.
Figure 8:
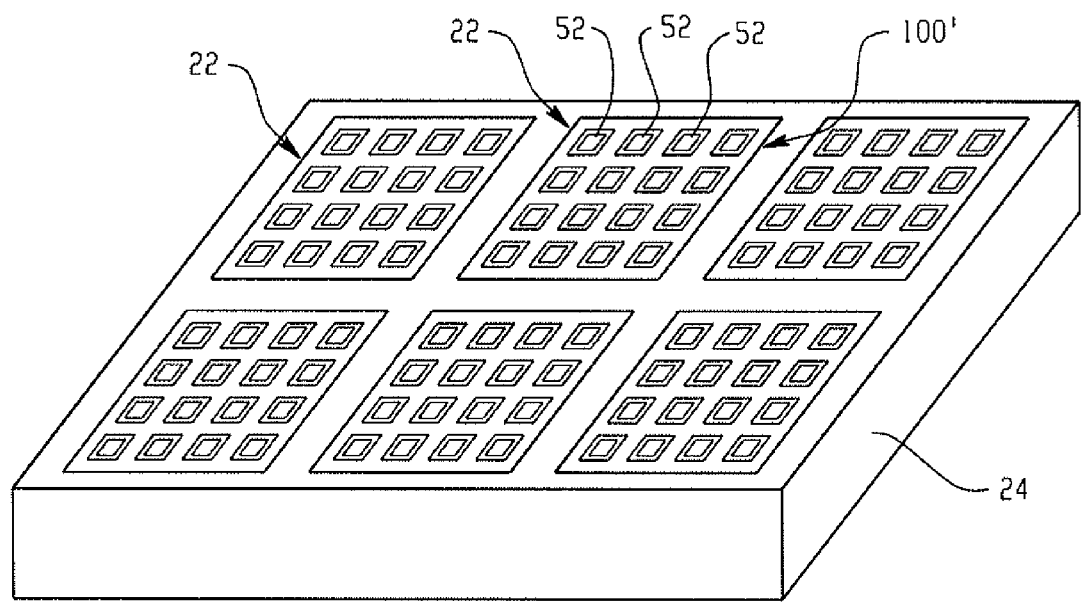
FIG. 8 shows a perspective view of another physical layout embodiment of the ixilated digital radiation detector, in which the photodiodes define a photodiode layer and the digital circuitry is disposed in the photodiode layer interspersed amongst the photodiodes.

With reference to FIGS. 7 and 8, in some embodiments the digital circuitry (such as the digital biasing circuitry 54, 54', 54", digital triggering circuitry 60, 60', 60", 84, and readout digital circuitry 66, 82) of the radiation detector 10 are defined by CMOS circuitry disposed on the silicon substrate 24. Various physical layouts can be used. In a vertically segregated layout shown in FIG. 7, the photodiodes 52 of the array of detector cells 50, 50', 50" define a photodiode layer 100, and the digital circuitry are disposed in a CMOS digital circuitry layer 102 separate from and electrically coupled with the photodiode layer 100. In an alternative layout shown in FIG. 8, the photodiodes 52 define a photodiode layer 100', and the CMOS digital circuitry (such as the digital biasing circuitry 54, 54', 54", digital triggering circuitry 60, 60', 60", 84, and readout digital circuitry 66, 82) are disposed in the photodiode layer 100' interspersed amongst the photodiodes 52.

Because CMOS logic draws power only when switching states, only those parts of the radiation detector 10 that are continuously actively clocked by the clock 88 will contribute to the baseline power consumption. Since the pixel 22 is activated by a trigger signal generated by one of the photodiodes 52 which are biased in the breakdown region in the quiescent state, power consumption is dependent on the photon detection rate and, thus, on the flux of received photons plus the dark count rate. Control of power consumption of the pixel 22 can be implemented by deliberately increasing the dead time of an individual pixel between two acquisitions. This could be done automatically by the pixel logic 80 depending on the temperature of the pixel. The temperature of the pixel can be measured directly by a temperature sensor (not shown) or estimated indirectly from the dark count rate of the pixel 22.

Since CMOS logic draws power only when switching states, the overall power consumption can be dramatically reduced by using a CMOS implementation over all analog implementation. For example, in some embodiments of an analog implementation, the power consumption per channel is 30 mW and the global part of the chip is 162 mW. For a more practical implementation, such as on a clinical apparatus with 28,336 channels or 1890 chips, the power consumption would be a constant 1156 W. On the other hand, the power consumption for a CMOS implementation, such as the various implementations described herein, has two different values, a static value and a dynamic value. The static power consumption is the power required when there are no counts and hence no switching of states. It does include power for the logic of for the dynamic switching as the logic must be ready to receive counts. The dynamic power consumption is the power required when the detector is actively receiving counts, and hence switching states. The power consumption in active state is dependent on the amount of activity; the more counts and switching of states, the power that is required. The static power consumption for a similar 1890 chip detector is about 10 W or less. The dynamic power consumption can vary, depending on the activity, but is typically about 300 W or less.

A problem can arise if the scintillation burst of light produces a flux of photons that is high enough to cause substantially all of the detector cells 50, 50', 50'' of one or more of the pixels 22 to transition from the first digital state to the second digital state during the integration time period. In this case, the pixel 22 saturates, and the actual intensity (that is, the flux of photons) is not accurately measured. This saturation problem can be addressed in various ways.

In one approach, the photosensitive area defined by the photodiodes 52 is broken into a larger number of smaller photodiodes. The reduced area of each photodiode reduces the likelihood that it will detect a photon. The larger total number of photodiodes provides higher pixel-level sensitivity to the flux of photons, although it generally does not fully compensate for the reduced area of each cell. The detector cells should have some separation to reduce optical crosstalk between neighboring detector cells. Typically, the separation of the cells is in the order of several microns or less, when trenches filled with opaque material are used for the separation. Thus, increasing the number of cells generally reduces the ratio of sensitive area to the total area of the cell to some degree. Additionally, increasing the number of detector cells, while keeping the cell size constant, typically leads to a proportional increase of the dark count rate.

Figure 9:
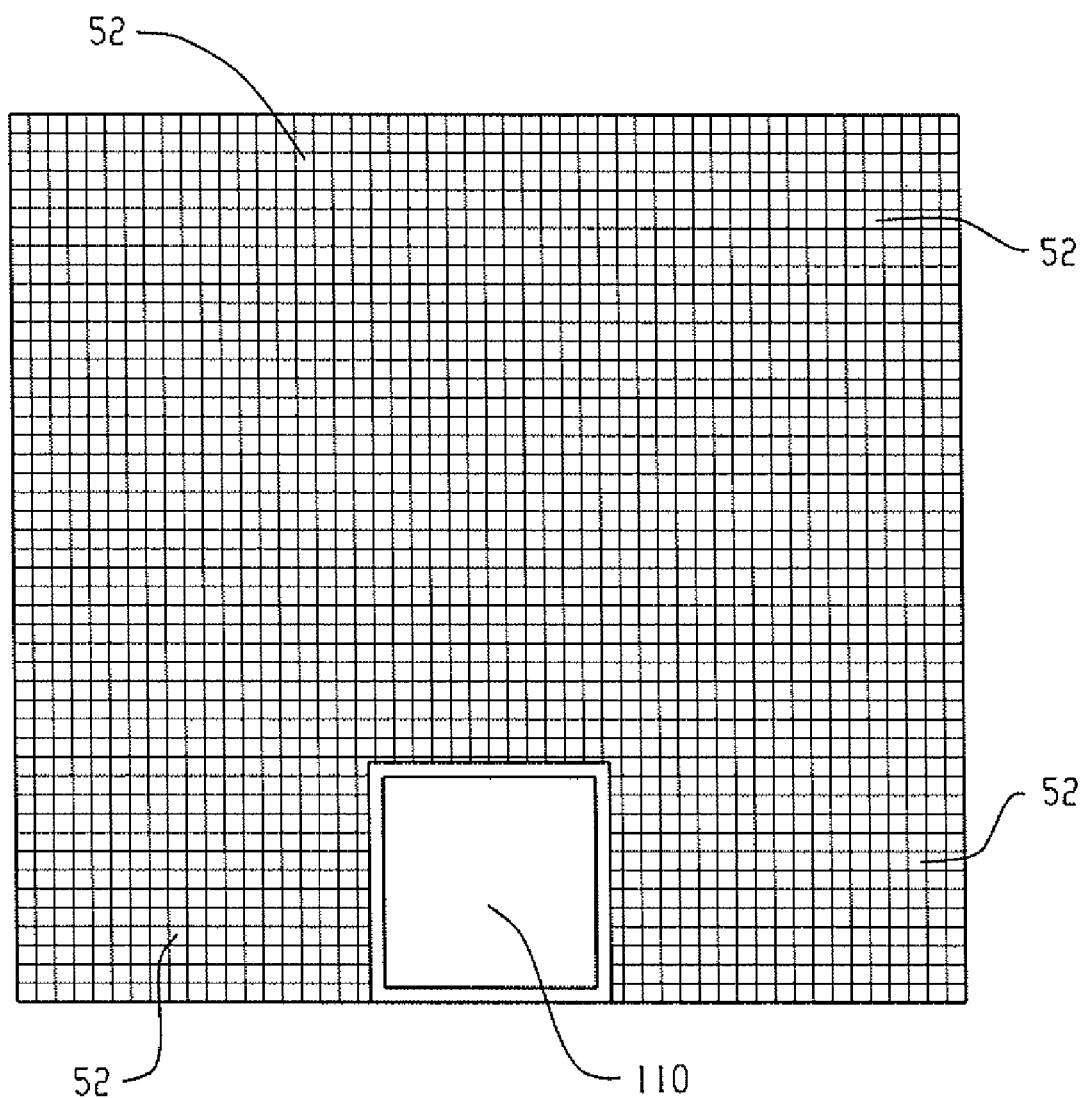
FIG. 9 shows a plan view of the light-sensitive area of a variant device which includes the ixilated digital radiation detector area and an additional proportional photodiode that produces an analog photocurrent when the flux of photons is high enough to saturate the ixilated digital radiation detector area.

With reference to FIG. 9, in another approach for addressing the saturation problem, a proportional photodiode 110 is included in the photosensitive area. The proportional photodiode 110 is larger than the photodiodes 52 used in digital detection. The proportional photodiode 110 is configured to produce an analog photocurrent proportional to the flux of photons impinging upon the pixel 22 when said flux of photons is high enough to cause substantially all of the detector cells 50, 50', 50'' of the pixel 22 to transition from the first digital state to the second digital state during the integration time period. Although shown along one side of the array of pixels 22 for simplicity of fabrication, the proportional photodiode 110 can be located in other positions respective to the array, such as centered in the array or at a corner of the array. Moreover, in some embodiments the proportional photodiode 110 may be distributed as a plurality of smaller electrically interconnected proportional photodiodes, such as a proportional photodiode located at each corner of the array of pixels 22. In the variation of FIG. 9, the trigger signal output by the first one of the photodiodes 52 to detect a photon is still suitably used to provide the timing information for the gamma ray detection event. Thus, the timestamp output by the radiation detector 10 is used; however, if the digital photodiodes 52 saturate, then the photocurrent produced by the proportional photodiode 110 is used to indicate photon flux intensity rather than using the digital count. The proportional photodiode 110 can be a conventional PIN diode, an avalanche photodiode with integrated analog or digital readout circuitry, or the like.

The pixelated digital radiation detectors are described herein in conjunction with an example TOF-PET application. However, the skilled artisan can readily adapt the disclosed pixelated digital radiation detectors for other application, such as single-photon emission computed tomography (SPECT) imaging, transmission computed tomography (CT) imaging, astronomy applications, and so forth. For radiation detection applications in which the photodiodes 52 are directly sensitive to the radiation, the scintillator 20 is suitably omitted from the radiation detector 10.

One skilled in the art should understand that while most of the embodiments have been described in conjunction with digital circuitry, portions of the invention can be implemented in conjunction with analog circuitry. For example, the following description provides a method of disabling defective cells in an analog circuitry system. Such embodiments are incorporated within the scope of this disclosure.

A defective cell disabling method for an analog circuit system can comprise of two separate stages, namely a sensing stage and a calibration stage. During the sensing stage, a SiPM array or device under test (DUT) is biased at the nominal bias voltage above threshold in a light-tight setup. The Geiger-discharge in semiconductors generates secondary light photons, approximately 3 per 100,000 electrons in the junction on average. Thus, a cell with gain 1,000,000 will generate about 30 optical photons. The average wavelength of these photons is about 1 $\mu$m, thereby enabling the photons to travel large distances in silicon before being absorbed. Some of these photons trigger breakdowns in neighboring cells, commonly referred to as optical crosstalk, if proper shielding is not used. Other photons can escape the silicon and can be detected by appropriate single photon detectors. The sensing detectors must be 1:1 coupled to the DUT cells. Thus, the trigger rate of the sensing detectors can then be directly associated with the dark count rate of individual cells. Additional measurement of the charge pulse of the DUT can be used to directly measure the gain and its variation for individual DUT cells. However to collect sufficient statistics, such measurement would likely mean a significant increase of the measurement time.

Based on the data acquired in the sensing stage, a laser beam will disable faulty cells. Additionally, the number of active cells per pixel can be adjusted to equalize the dynamic range of the pixels, if required. In some implementations, a fuse is used to disable the faulty cells. While a fuse would undesirably consume additional area, this can be minimized if the fuse is placed over the guard ring. Another alternative would be to cut the poly resistor itself.

Figure 10:
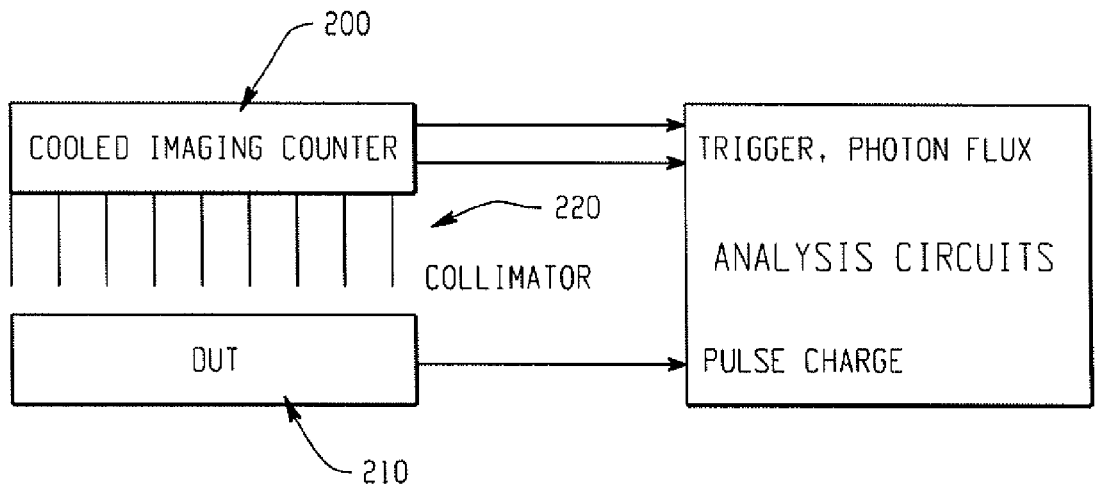
FIG. 10 shows an illustrative example of the measurement setup used in the first stage of a defective cell disablement process for detectors including analog circuitry.
Figure 11:
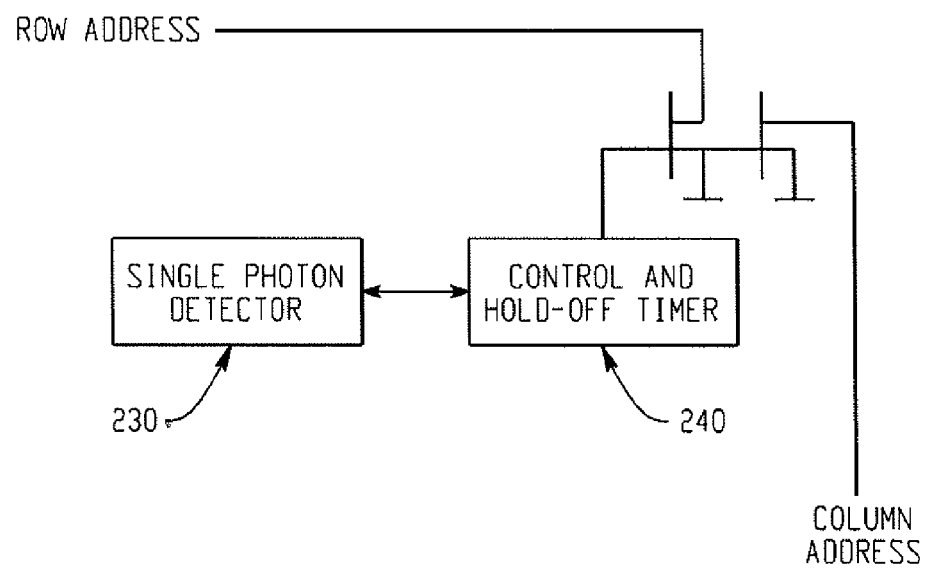
FIG. 11 shows a block schematic of one imaging counter cell.
Figure 12:
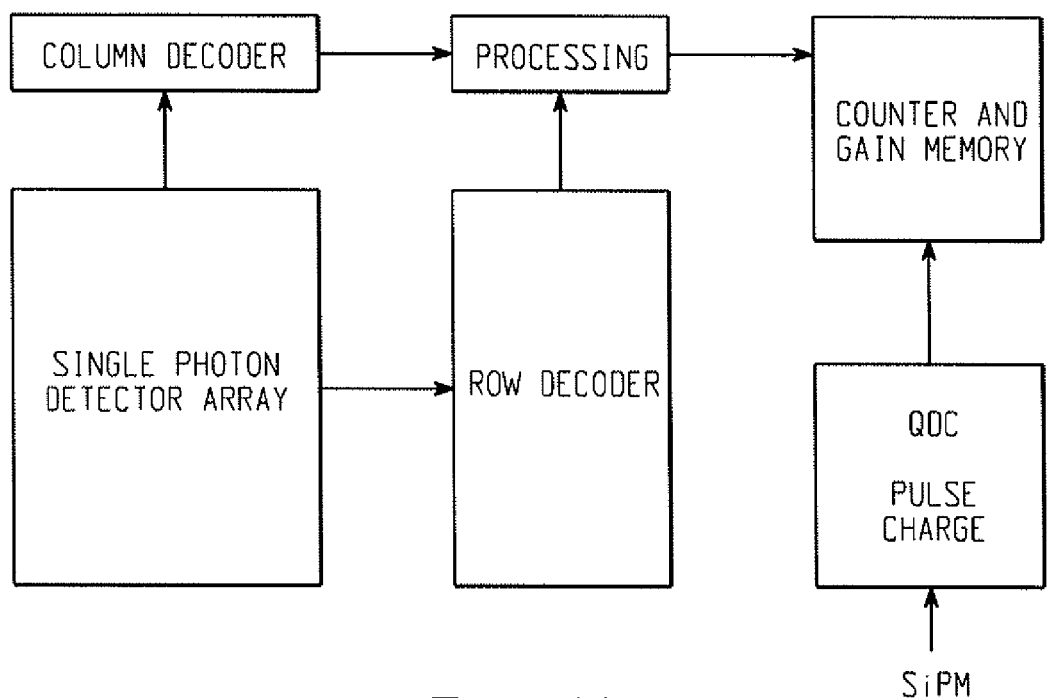
FIG. 12 shows a sensor block diagram.

An illustrative example of the measurement setup used in the first stage is shown in FIG. 10. In FIG. 10, a single photon counter array 200 is 1:1 coupled to the DUT 210 using a collimator structure 220. One skilled in the art should understand that if the sensing detector has the same pixel size as the DUT, proximity coupling could be used to increase the sensitivity of the system. The single photon counter array 200 must have significantly lower dark count rate and thus has to be cooled down to at least −50° C. Each detector 230 in the photon counter array 200 is triggered by photons emitted by the Geiger-mode discharge. The detector indicates the event by pulling down the row and column lines and starting a hold-off interval to avoid double counting of the same event. The length of the hold-off interval must be adjusted to the recovery time of the DUT. An active quenching/recharge circuit 240 can be used to obtain well-defined hold-off intervals. Additional circuits can be used to measure the charge of the pulse in correlation to the coordinates of the event. A block schematic of one imaging counter cell is shown in FIG. 11, while a sensor block diagram is shown in FIG. 12.

Figure 13:
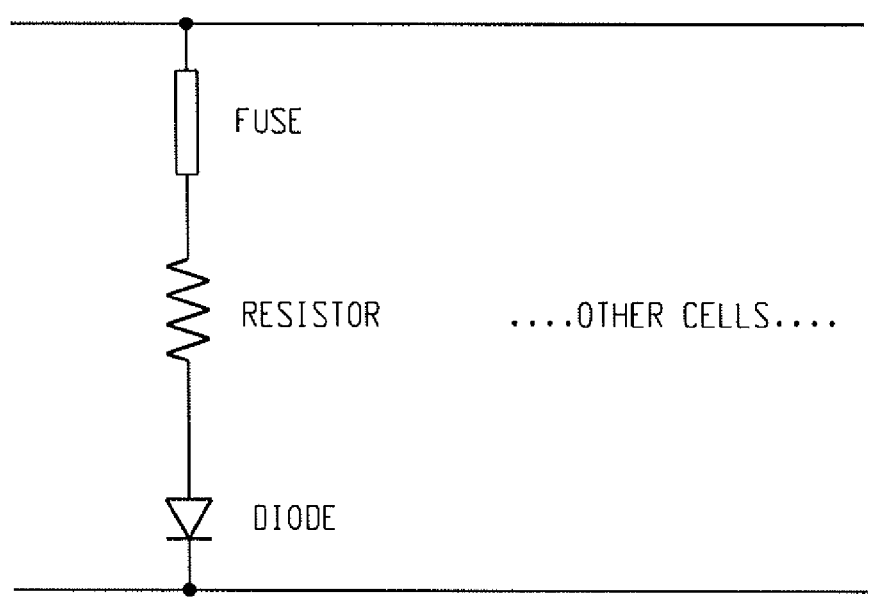
FIG. 13 shows a photodetector incorporating a fuse for disablement.

Increasing the DUT temperature can be used to accelerate the measurement. In the calibration stage, the pixel dark count rate and gain data is used to select a subset of cells that will be disabled. This can be any number of defective cells as well as other cells that can be disabled to provide uniformity. To achieve this, a laser is used to cut the fuses in these cells, as illustrated in the modified detector cell shown in FIG. 13.

Regardless of whether a digital or analog disablement process is used, a report can be generated allowing a user to determine how many cells were disabled because they were deemed faulty. The report can further provide the location of the disabled faulty cells. The location of the disabled faulty cells can, in some embodiments, be used to disable other cells. Typically this would be done in some sort of geometrical pattern to allow for more uniform detection of radiation about the detector. Furthermore, the disablement of other cells can be automatic, in response to manual input or feedback, or a combination thereof.

The resulting silicon photomultiplier array will have lower dark count rate at the expense of decreased sensitivity because of the area lost due to dead cells. The loss in dynamic range can be accounted for beforehand by integrating higher number of smaller-sized cells in the pixels. It should also be appreciated that the fuse implementation can be used in combination with digital circuitry. For example, the fuse can be used for calibration, while the digital circuitry is used for the count detection. Other embodiments incorporating these types of ideas are also contemplated by this disclosure.

In some embodiments in which a trigger at the single photon level is not needed, a leading edge discriminator can be used to generate the trigger signal and to suppress dark counts. In other embodiments the trigger signal can be generated digitally by applying a logical operation on the trigger lines. For example, a pixel can be subdivided into two halves, or blocks, and the trigger signal is only generated if both halves detect the photon.

In such embodiments, the number and size of the blocks can be adjusted to set the average threshold and the selectivity. Of course, other similar designs can be implemented, including, but not limited to, other geometries and other ways of correlating pixel blocks.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having described the preferred embodiments, the invention is now claimed to be:

1. A detector pixel for use in conjunction with a scintillator that converts a radiation particle to a burst of light, the detector pixel comprising:
    an array of detector cells, each detector cell including a photodiode biased in a breakdown region and digital circuitry coupled with the photodiode, the digital circuitry being configured to output a first digital value in a quiescent state and a second digital value responsive to detection of a photon by the photodiode;
    digital triggering circuitry configured to output a trigger signal indicative of a start of an integration time period responsive to a selected number of one or more of the detector cells transitioning from the first digital value to the second digital value;
    readout digital circuitry that accumulates a count of a number of transitions of detector cells of the array of detector cells from outputting the first digital value to outputting the second digital value over the integration time period;
    a proportional photodiode configured to produce an analog photocurrent proportional to a flux of photons impinging upon the detector pixel; and
    digital time stamp circuitry connected to the array of detector cells to create a timestamp based on a time of the trigger signal that indicates a time of receipt of the flux of photons.

2. The detector pixel as set forth in claim 1, wherein each detector cell further includes:
    quenching circuitry configured to transition the detector cell back to the quiescent state after detection of a photon by the photodiode.

3. The detector pixel as set forth in claim 1, further including:
    trigger validation circuitry that monitors a current in the detector pixel and aborts the accumulation of the count responsive to an abort criterion.

4. The detector pixel as set forth in claim 1, wherein the readout digital circuitry includes:
    a buffer associated with each detector cell that buffers the second digital value; and
    pixel level readout circuitry configured to sequentially accumulate the buffers associated with the detector cells having the second digital value to produce the count.

5. The detector pixel as set forth in claim 1, wherein the readout digital circuitry includes:
    an accumulator associated with each detector cell, each accumulator configured to accumulate transitions of the associated detector cell from outputting the first digital value to outputting the second digital value over the integration time period; and
    adding circuitry that sums the values stored in the accumulators at the end of the integration time period to produce the count.

6. The detector pixel as set forth in claim 1, wherein the digital triggering circuitry is configured to output a trigger signal indicative of a start of an integration time period responsive to a single detector cell transitioning from the first digital value to the second digital value.

7. The detector pixel as set forth in claim 1, wherein the digital triggering circuitry is configured to output a trigger signal indicative of a start of an integration time period responsive to a plurality of detector cells transitioning from the first digital value to the second digital value producing a current exceeding a selected triggering current level.

8. The detector pixel of claim 1, wherein the photodiodes of the array of detector cells define a photodiode layer and the digital circuitry forms a digital circuitry layer separate from and electrically coupled to the photodiode layer.

9. The detector pixel of claim 1, wherein the photodiodes of the array of detector cells define a photodiode layer and the digital circuitry is disposed in the photodiode layer at least partially interspersed amongst the plurality of photodiodes.

10. A radiation detector comprising:
    a scintillator; and
    an array of detector pixels as set forth in claim 1 arranged to receive bursts of light produced by the scintillator in response to received radiation.

11. The radiation detector as set forth in claim 10, wherein the array of detector pixels are disposed monolithically on a common silicon substrate.

12. The radiation detector as set forth in claim 11, wherein (i) the photodiodes of the array of detector cells define a photodiode layer, and (ii) the digital circuitry, digital triggering circuitry, and readout digital circuitry define a digital circuitry layer separate from and electrically coupled with the photodiode layer.

13. The radiation detector as set forth in claim 11, wherein (i) the photodiodes of the array of detector cells define a photodiode layer, and (ii) the digital circuitry, digital triggering circuitry, and readout digital circuitry are disposed in the photodiode layer interspersed amongst the photodiodes.

14. The radiation detector as set forth in claim 11, wherein at least a substantial portion of the digital circuitry, digital triggering circuitry, and readout digital circuitry are CMOS circuitry.

15. The radiation detector as set forth in claim 11, further including:
  multiplexing circuitry also disposed monolithically on the common silicon substrate, the multiplexing circuitry digitally multiplexing counts produced by the readout digital circuitry of the detector pixels to generate a digital radiation detector output signal.

16. A time of flight positron emission tomography imaging system comprising:
  a plurality of radiation detectors as set forth in claim 10 disposed to detect gamma rays emitted from an imaging region;
  gamma ray pair detection circuitry that identifies two substantially simultaneous gamma ray detections by two of the radiation detectors;
  a line of response processor that determines a spatial line of response connecting the two gamma ray detections; and
  a time of flight processor that localizes a positron electron annihilation event along the line of response based on a time difference between the two substantially simultaneous gamma ray detections.

17. The radiation detector as set forth in claim 10, wherein said digital circuitry operates in a static power consumption mode when there are no photodiode events and operates in a dynamic power consumption mode when there are photodiode events.

18. The radiation detector as set forth in claim 10, wherein power consumption required by the radiation detector is at least approximately one third of the power consumption required by an analogous detector with circuitry that provides analog values in response to photodiode events.

19. A method performed in conjunction with a scintillator that converts a radiation particle to a burst of light, the method comprising:
  switching digital circuitry from a first digital value to a second digital value responsive to detection of a photon by a photodiode biased in a breakdown region, the switching defining a switching event;
  generating a trigger signal indicative of a start of an integration time period responsive to a selected number of one or more said switching events associated with a plurality of said photodiodes;
  accumulating a count of switching events associated with the plurality of said photodiodes over the integration time period; and
  generating an analog photocurrent proportional to a flux of photons using a separate proportional photodiode when said flux of photons is high enough to cause substantially all of the photodiodes to participate in switching events during the integration time period.

20. The method as set forth in claim 19, further including:
  subsequent to a switching event, quenching the photodiode back to a quiescent state corresponding to the first digital value.

21. The method as set forth in claim 19, further including:
  monitoring the accumulating; and
  aborting the accumulating responsive to occurrence of an abort criterion determined by the monitoring.

22. The method as set forth in claim 19, further including:
  generating a digital timestamp associated with the accumulating over the integration time period, the digital timestamp being based on a time of generation of the trigger signal and a reference time signal.

23. The method as set forth in claim 22, further including:
  repeating the generating of the trigger signal indicative of the start of an integration time period, the accumulating of the count over the integration time period, and the generating of a digital timestamp associated with the count to generate a plurality of counts each having an associated digital timestamp; and
  sorting the counts according to their associated digital timestamps to produce a stream of event data sorted over time.

24. A radiation detector including a scintillator and circuitry for performing the method set forth in claim 19.

25. The method of claim 19, further comprising disabling selected photodiodes by sensing the dark count rate of individual photodiodes of the plurality of photodiodes and determining which photodiodes are defective based on the dark counts sensed and using a laser to cut a fuse associated with the photodiodes determined to be defective.

26. The method of claim 25 further comprising
  determining the location of the defective photodiodes; and
  disabling one or more non-defective photodiodes based on the location of the defective photodiodes.

27. A radiation detector including a scintillator and circuitry for performing the method set forth in claim 19.

* * * * *

UNITED STATES PATENT AND TRADEMARK OFFICE
CERTIFICATE OF CORRECTION

PATENT NO. : 7,723,694 B2
APPLICATION NO. : 11/467670
DATED : May 25, 2010
INVENTOR(S) : Frach et al.

It is certified that error appears in the above-identified patent and that said Letters Patent is hereby corrected as shown below:

On the Title Page add the following:

Related U.S. Application Data

(63) Continuation of PCT/IB2006/051089, filed on April 10, 2006.

(60) Provisional application No. 60/674,034, filed on April 22, 2005; and
Provisional application No. 60/682,246, filed on May 18, 2005.

Signed and Sealed this
Third Day of April, 2012

David J. Kappos
*Director of the United States Patent and Trademark Office*